United States Patent
Jacobsen

(10) Patent No.: US 10,687,756 B1
(45) Date of Patent: Jun. 23, 2020

(54) RISK TOLERANCE SIMULATION AND BASELINE

(71) Applicant: Wells Fargo Bank, N.A., San Francisco, CA (US)

(72) Inventor: Brian J. Jacobsen, Elm Grove, WI (US)

(73) Assignee: Wells Fargo Bank, N.A., San Francisco, CA (US)

( * ) Notice: Subject to any disclaimer, the term of this patent is extended or adjusted under 35 U.S.C. 154(b) by 682 days.

(21) Appl. No.: 15/362,489

(22) Filed: Nov. 28, 2016

(51) Int. Cl.
| A61B 5/00 | (2006.01) |
|---|---|
| A61B 5/16 | (2006.01) |
| A61B 5/01 | (2006.01) |
| A61B 5/024 | (2006.01) |
| A61B 5/1455 | (2006.01) |
| G16H 40/63 | (2018.01) |
| A61B 90/50 | (2016.01) |

(52) U.S. Cl.
CPC .............. *A61B 5/4884* (2013.01); *A61B 5/01* (2013.01); *A61B 5/02416* (2013.01); *A61B 5/1455* (2013.01); *A61B 5/165* (2013.01); *A61B 5/7445* (2013.01); *G16H 40/63* (2018.01); *A61B 2090/502* (2016.02); *A61B 2503/12* (2013.01)

(58) Field of Classification Search
CPC ..... A61B 5/4884; A61B 5/01; A61B 5/02416; A61B 5/1455; A61B 5/165; A61B 5/7445; G16H 40/63
USPC ........................................................ 600/558
See application file for complete search history.

(56) References Cited

U.S. PATENT DOCUMENTS

| 6,425,764 | B1 | 7/2002 | Lamson |
| 7,231,608 | B1 | 6/2007 | Fano et al. |
| 8,407,125 | B2 | 3/2013 | Jenson et al. |
| 9,104,235 | B2 | 8/2015 | Brancato et al. |
| 2005/0015296 | A1 | 1/2005 | Dougan |
| 2005/0154662 | A1 | 7/2005 | Langenwalter |
| 2006/0031149 | A1 | 2/2006 | Lyons |
| 2006/0079803 | A1* | 4/2006 | Poreh ..................... A61B 5/162 600/558 |
| 2006/0212380 | A1* | 9/2006 | Williams ............... G06Q 40/00 705/35 |
| 2008/0081963 | A1 | 4/2008 | Naghavi et al. |

(Continued)

FOREIGN PATENT DOCUMENTS

WO    WO-2013172809 A2    11/2013

*Primary Examiner* — Daniel L Cerioni
(74) *Attorney, Agent, or Firm* — Schwegman Lundberg & Woessner, P.A.

(57) ABSTRACT

A system includes a biometric sensor configured to detect physiological data associated with anxiety of a user, a memory, and at least one hardware processor executing operations. The operations include selecting a plurality of stimuli from a pool of stimuli, the selected plurality of stimuli including at least one target stimuli associated with a subject matter and at least one generic stimuli not directly associated with the subject matter. The operations also include presenting each stimulus to the user, collecting sensor readings from the biometric sensor, and generating anxiety results. The operations also include determining an anxiety score based on the anxiety results, identifying a plurality of risk tolerance ranges, each risk tolerance range being associated with a category of risk tolerance, and determining a risk tolerance result of the user based on comparing the anxiety score to the plurality of risk tolerance ranges.

20 Claims, 7 Drawing Sheets

(56) References Cited

U.S. PATENT DOCUMENTS

| | | |
|---|---|---|
| 2008/0214903 A1 | 9/2008 | Orbach |
| 2011/0270780 A1 | 11/2011 | Davies et al. |
| 2012/0278258 A1* | 11/2012 | Ayal .................. G06Q 40/00 705/36 R |
| 2014/0025605 A1 | 1/2014 | Salter |
| 2014/0081768 A1 | 3/2014 | Hocking, Jr. et al. |
| 2014/0129480 A1 | 5/2014 | LeRose et al. |
| 2014/0347265 A1 | 11/2014 | Aimone et al. |
| 2014/0349261 A1* | 11/2014 | Dennis .................. G09B 5/02 434/236 |
| 2015/0039443 A1 | 2/2015 | Soon-Shiong |
| 2015/0348162 A1 | 12/2015 | Morris et al. |
| 2016/0077547 A1 | 3/2016 | Aimon et al. |
| 2017/0003507 A1* | 1/2017 | Raval .................. G02B 27/0172 |
| 2017/0119295 A1* | 5/2017 | Twyman ................ A61B 3/112 |
| 2017/0281026 A1* | 10/2017 | Nick .................. A61B 5/02416 |

* cited by examiner

US 10,687,756 B1

RISK TOLERANCE SIMULATION AND BASELINE

TECHNICAL FIELD

Embodiments described herein generally relate to simulation systems and, for example and without limitation, to systems and methods for evaluating risk tolerance using computer-based simulations.

BACKGROUND

Many people experience nervousness and anxiety at differing levels based on certain stimuli. Some are more stalwart, not as easily stressed by a given event. Others may tend to be more anxiety-prone, experiencing greater nervousness in response to that same event. Further, an expanding market for wearable computing devices and wearable sensors has made collection of real-time biometric data about themselves more accessible to people, as well as the computing systems they might use in their daily lives.

BRIEF DESCRIPTION OF THE SEVERAL VIEWS OF THE DRAWINGS

In the drawings, which are not necessarily drawn to scale, like numerals may describe similar components in different views. Like numerals having different letter suffixes may represent different instances of similar components. Some embodiments are illustrated by way of example, and not of limitation, in the figures of the accompanying drawings, in which.

DETAILED DESCRIPTION

Figure 1:
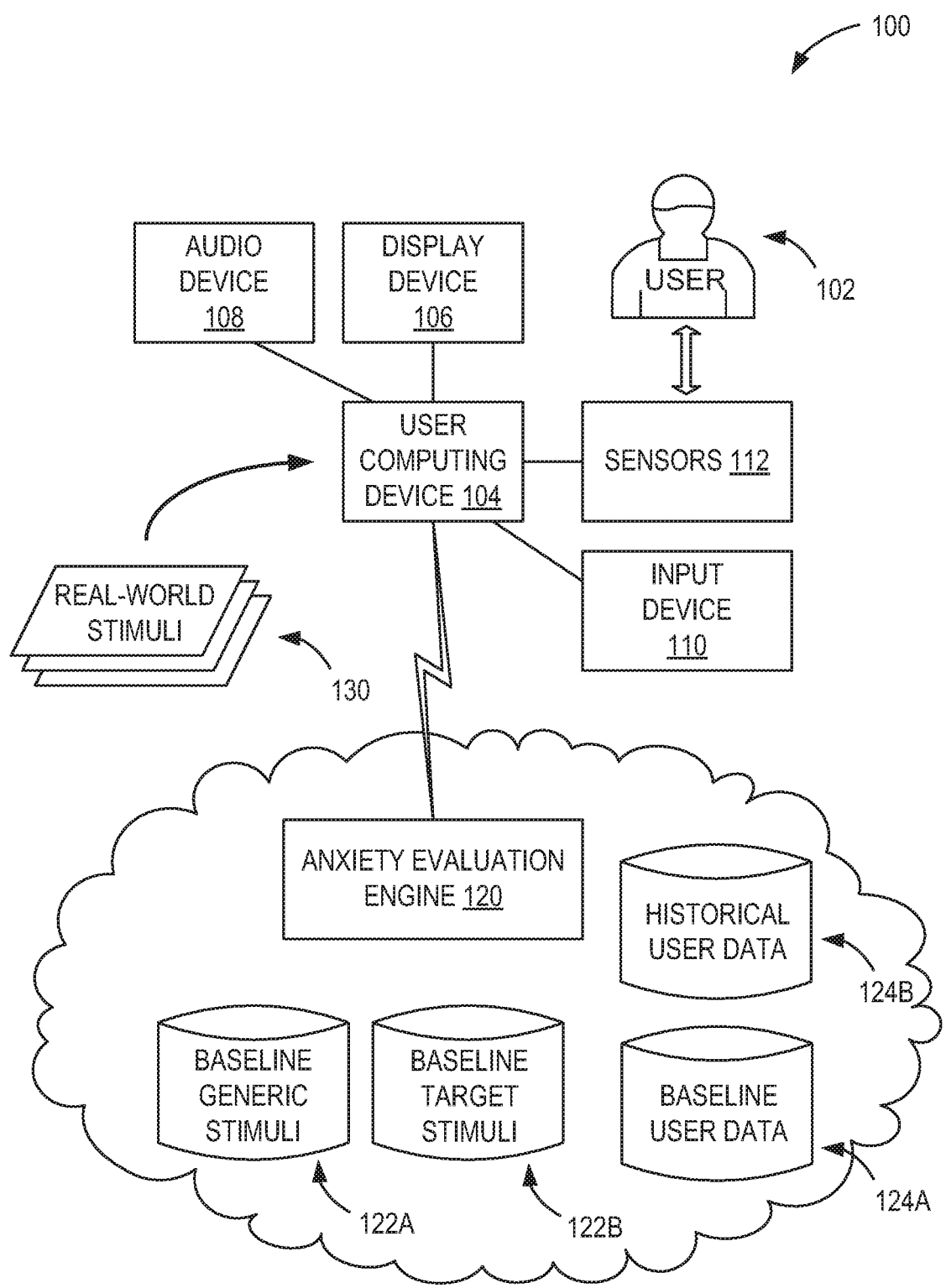
FIG. 1 illustrates an example networked environment including components of an anxiety evaluation system for evaluating risk tolerance of a user.

The systems and methods described herein, for example, describe a technical solution for evaluating a user's tolerance for risk using computer-based simulation, baseline metrics, and real-world data. An anxiety evaluation system is described herein. The anxiety evaluation system collects biometric sensor data for a user that may be used to evaluate the user's anxiety level in various situations. The anxiety evaluation system uses the anxiety data to evaluate the user's relative tolerance for risk.

In one example embodiment, the anxiety evaluation system performs baseline data collection for the user by presenting the user with various pre-selected visual and auditory "baseline stimuli" configured to elicit a range of responses. As the user experiences the baseline stimuli (e.g., images of kittens at play, or a video of a frightening monster, or audio of a car chase with screeching breaks), the system collects biometric sensor data from the user. Biometric sensors measure physiological changes in the user while experiencing the stimuli. The anxiety evaluation system evaluates the biometric sensor data as a proxy for anxiety (e.g., stress, nervousness, excitement) in the user. Based on the baseline stimuli, the anxiety evaluation system places the various responses of the user on an "anxiety scale" (e.g., a raw value based on sensor data inputs, or a normalized value, such as between 1 and 100). For example, one stimuli may generate the lowest score on the anxiety scale, another the highest score, and the rest may fall somewhere between. The anxiety system may compute a median, mean, average, low, high, and range of anxiety scores for the user, which may subsequently be used to evaluate aspects of risk tolerance for the user.

In some embodiments, a subset of the baseline stimuli ("target baseline stimuli") are related to a particular "target" subject matter, where the rest of the "generic" baseline stimuli are related to other subject matter. The anxiety analysis system distinguishes the target stimuli from the generic stimuli and, as such, may generate anxiety scores separately. In other words, the user may have an anxiety range or an anxiety average for the generic stimuli that is different from their anxiety range or anxiety average when experiencing the target stimuli. As such, differences in generic values over target subject matter values may indicate certain things about the user relative to the target subject matter. For example, if the user's average target anxiety score is higher than their average generic anxiety score, this may be an indication that the user exhibits a greater sensitivity to the target subject matter. On the other hand, if the user's average target anxiety score is lower, then this may be an indication that the user is less susceptible to the target subject matter.

In some embodiments, the anxiety analysis system may provide the baseline stimuli to the user with augmented reality (AR) or virtual reality (VR) using a head-mounted display (HMD). The user would, thus, experience a virtual environment (in the case of VR) or a mixed environment (in the case of AR), thereby providing a more immersive environment through which the baseline stimuli may be delivered. Some of the biometric sensors providing the anxiety data may be captured from wearable devices worn by the user. For example, the user may wear a wrist device (e.g., watch), or the HMD, or an implant having biometric sensors, or similar devices. Such devices may provide convenience and ubiquity of use by enabling anxiety data collection outside of traditional clinical settings.

FIG. 1 illustrates an example networked environment including components of an anxiety evaluation system 100 for evaluating risk tolerance of a user 102. In an example embodiment, the anxiety evaluation system 100 includes an anxiety evaluation engine 120 communicatively coupled to a user computing device 104. In some embodiments, the anxiety evaluation engine 120 may be executed by the user computing device 104, or may be executed by another computing device. The user 102 is the subject of various biometric evaluations, as described herein. The anxiety evaluation engine 120 receives sensor data of the user 102 measuring aspects of physiological change related to anxiety (e.g., stress, nervousness, excitement, distress) and, from this biometric data, evaluates the user 102 with regard to risk tolerance (e.g., the user 102's comfort for taking risks).

In an example embodiment, the user computing device 104 is communicatively coupled to a display device 106 (e.g., used for presenting visual outputs to the user 102), an audio device 108 (e.g., speakers for presenting audio outputs to the user 102), one or more input devices 110 (e.g., keyboard, mouse, hand-held controller(s), motion tracking controller, microphone, digital camera, and so forth), and one or more sensors 112 (e.g., biometric sensors, digital camera, inertial sensors, global positioning system (GPS) sensors, and so forth). In some embodiments, one or more of the display device 106, audio device 108, sensors 112, and input device 110 are part of the user computing device 104. In some embodiments, the user computing device 104 may include a smartphone, tablet, laptop, an HMD or other wearable computing device, or a desktop computer. The display device 106 may be, for example, a conventional flat-screen monitor, or one or more eye displays of a VR or AR HMD.

In an example embodiment, at least one of the sensors 112 includes a biometric sensor configured to measure physiological aspects of the user 102 for use in evaluating anxiety of the user 102. For example, sensors 112 may include an optical or infrared image sensor of a digital camera device which may be configured to capture digital video or still images of a face of the user 102 as the user 102 experiences various stimuli. The anxiety evaluation engine 120 may analyze facial features (e.g., expressions and changes in expression) of the user 102 using the digital video or images in order to detect aspects of anxiety. Sensors 112 may include electrodermograph (EDG) or electrodermal (EDA) sensors which measure skin electrical and electrodermal activity using galvanic skin response (GSR), which may be used, for example, as an indicator of anxiety (e.g., stress). Sensors 112 may include photoplethysmographic (PPG) sensors for measuring blood flow, heart rate, heart rate variability, and so forth. Sensors 112 may include thermistor sensors for detecting skin temperature. Sensors 112 may include spectrometers or molecular sensors to detect changes in body chemistry or hormonal changes.

During operation, the anxiety evaluation engine 120 presents the user 102 with various stimuli 122A, 122B (collectively, baseline stimuli 122) via the user computing device 104, and collects various physiological responses of the user 102 from the sensors 112. Stimuli 122 may include digital content such as, for example, text-based content (e.g., news articles, books, blogs), static images, two-dimensional (2D) videos, immersive 2D or three-dimensional (3D) environments, or audio outputs. Stimuli 122 may include gustaoception, olfacoception, and tactioception. Some stimuli 122 may be presented to the user 102 via the display device 106, or via the audio device 108. Some of the stimuli 122 may allow interaction by the user 102 (e.g., via the input devices 110), such as through 2D or 3D environments (e.g., gaming-type environments). The baseline stimuli 122 are presented to the user 102 one at a time during a baseline process. In some embodiments, the baseline generic stimuli 122A may be presented to the user 102 separate from the baseline target stimuli 122B. In other embodiments, the generic stimuli 122A and target stimuli 122B may be mixed together.

In an example embodiment, baseline stimuli 122 are categorized as baseline target stimuli 122B or baseline generic stimuli 122A. Baseline target stimuli 122B include digital content related to a particular "target" subject matter. For example, if the target subject matter is "airplanes", then the baseline target stimuli 122B may include a news article about development of a new plane, pictures or videos involving various aircraft, videos of takeoffs and landings, stunt planes performing acrobatic maneuvers, crowded airline flights, war planes in combat, terrorists hijacking a plane, crash landings, or audio of a jet engine or of an airplane crash. Baseline generic stimuli 122A may include digital content not directly related to the target subject matter. For example, baseline generic stimuli 122A may include pictures or videos of a seascape, a snowy mountain peak, a smiling baby, a long line at a grocery store, an ambulance blaring emergency sirens, two professional fighters punching each other, or a car accident.

In an example embodiment, each particular baseline stimulus 122 is pre-identified (e.g., by an analyst) and staged for presentation to the user 102 during the baseline process. The analyst may select (e.g., through a user interface such as a web browser or other front-end application) a range of stimuli 122 for each of the generic stimuli 122A and the target stimuli 122B that may generally elicit a range of anxiety in users 102. For example, many users 102 may exhibit little anxiousness in response to a picture of an airplane, or of a snowy mountain peak, as they are both generally pleasant to view. Many users 102 may exhibit some anxiety when viewing other digital content such as a crowded airline flight or a long line at a grocery store, as they may empathize with having to experience a long delay. Many users 102 may experience greater anxiety when viewing digital content such as an airplane crash or a car accident, as they may appreciate the inherent dangers to passengers in those situations.

In some embodiments, baseline stimuli 122 may include one or more sensor timing marks. A sensor timing mark for a particular stimulus identifies a time, during presentation of that stimulus, at which sensor readings are taken. In other words, sensor data may be collected at particular points during the presentation of a stimulus, as identified by sensor timing marks. Some stimuli 122 may tend to exhibit greatest effect (e.g., highest anxiety) at a particular point during presentation. For example, a video of a rollercoaster may include several sensor timing marks as the viewer ascends up to the top of the rollercoaster (e.g., likely exhibiting some mild anxiety during such time) and may include additional sensor timing marks as the viewer crests and begins the first big descent (e.g., likely exhibiting high anxiety).

During the baseline process, the anxiety evaluation engine 120 presents these baseline stimuli 122 to the user 102 and contemporaneously collects anxiety readings from the sensors 112. In an example embodiment, these baseline anxiety readings are associated with the user 102 and stored as baseline user data 124A. Each baseline anxiety reading (e.g., raw sensor value, or a normalized sensor value) is associated with a type of sensor (e.g., identifying what type of physiological value it is), a particular baseline stimulus 122, a category (e.g., generic stimulus 122A or target stimulus 122B), and the particular user 102. The collection of baseline anxiety readings from the baseline stimuli 122 are used as a "baseline profile" (not separately depicted in FIG. 1) of the user 102. The baseline profile may be used to evaluate risk tolerance of the user 102, as described in further detail below.

In some embodiments, each stimulus 122 may have been presented to many users 102 over time, and the historical responses of each presentation of the stimulus 122 to the various users 102 may be stored and later used for various computations and comparisons across users 102. In some examples, not every stimulus 122 is shown to each user. In other words, baseline profiles for many users 102 may be used by the anxiety evaluation engine 120 to compare users 102 to each other, such as for anxiety results comparisons to an average.

Further, in an example embodiment, the user 102 may also experience various real-world stimuli 130 via the user computing device 104. Real-world stimuli 130 represent experiences that are not pre-determined, but are instead generated by real-world events. For example, and continuing the above example, the user 102 may be using their user computing device 104 to consume news articles or other digital content from various news sources, and may read a recent article about a plane crash, or may watch a video and commentary on the plane crash. Some real-world stimuli 130 may be about the target subject matter, while other real-world stimuli 130 may be generic. In some embodiments, the anxiety evaluation engine 120 may evaluate the contents of the real-world stimuli 130 relative to the target subject matter, determining whether or not the real-world stimuli 130 is related to the target subject matter, or whether the real-world stimuli 130 is generic (e.g., via text processing of text content, speech recognition of audio, image recognition). Real-world stimuli 130 may be categorized statistically based on, for example, comparing sensor readings across a number of users. This allows for relative comparisons to see whether a particular user is more or less sensitive to certain stimuli, and may allow for clustering and categorizing types of users.

While experiencing such real-world stimuli 130, the user computing device 104 captures real-world anxiety readings of the user 102 from the sensors 112, similar to what is described above with regard to data collection for baseline stimuli 122. In an example embodiment, the anxiety evaluation engine 120 receives the real-world anxiety readings and, in some embodiments, digital content associated with the real-world stimuli 130 from the user computing device 104. The data associated with real-world stimuli 130 is stored as historical user data 124B, with data and associations similar to the baseline user data 124A as described above, and may be used for analyzing risk tolerance of the user 102, as described in greater detail below. In some sense, real-world stimuli 130 may present a more authentic evaluation of anxiety response in the user 102 because, for example, the real-world stimuli 130 is not a simulation, and the real-world stimuli 130 may be experienced in closer proximity to some underlying real-world event (e.g., a short time later).

Real-world stimuli 130 events may be presented in a training session. Further, such session stimuli may be periodically updated, such as through regular monitoring of the user 102 while they are connected to a biometric sensor. Alternatively, the real-world context may be evaluated periodically or randomly with biometric measurements taken concurrently. For example, sensors 112 may detect a state change in the user 102 (e.g., a sudden change in heart rate), which may trigger capturing and recording the current real-world stimuli 130 being experienced by the user 102 at that time (e.g., via video or audio capture, screen capture of a computing device they are currently using, and so forth).

Figure 2:
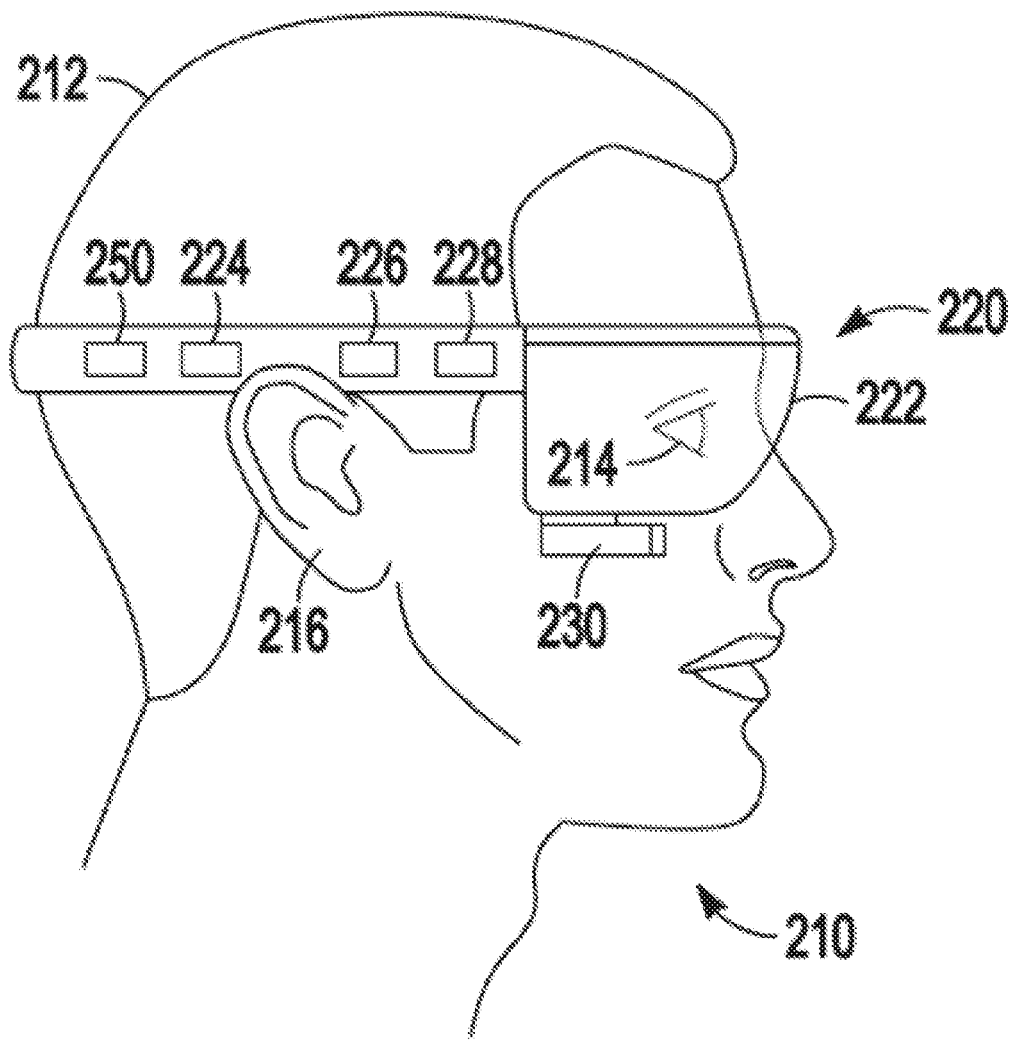
FIG. 2 illustrates an example head-mounted display (HMD) device shown in a mounted configuration on a head of a wearer (or "user")

FIG. 2 illustrates an example HMD device 220 shown in a mounted configuration on a head 212 of a wearer (or "user") 210. In the example embodiment, the HMD device 220 includes an opaque visor 222 which may obscure the wearer 210's view of the real world, but may present the wearer 210 a view of their surroundings via input from a digital camera device 230. The visor 222 is depicted as transparent in FIG. 2 for purposes of illustration. In other embodiments, the HMD device 220 may include a transparent or semi-transparent visor (or "lens", or "lenses") 222 through which the wearer 210 may view their surroundings (also herein referred to also as "the real world", or an "environment"). The HMD device 220 also includes a display device 228 that renders graphics (e.g., digital images) on the visor 222. In some embodiments, the display device 228 projects images onto the visor 222. As such, the visor 222 acts as a "screen" or surface on which the output of the display device 228 appears, and through which the wearer 210 experiences digital content such as the stimuli 122, 130 shown in FIG. 1. In some embodiments, the wearer 210 may be similar to the user 102, the HMD device 220 may be similar to the user computing device 104, or the display device 228 and visor 222 may be similar to the display device 106.

The display device 228 is driven or controlled by one or more graphics processing units (GPUs) 226. The GPU 226 processes aspects of graphical output that assists in speeding up rendering of output through the display device 228. The HMD device 220 also includes a central processor 224 that may execute some of the operations and methods described herein. The HMD device 220 also includes an audio device 250 that is configured to present audio output to the wearer 210 (e.g., via ears 216).

In some embodiments, the HMD device 220 includes the digital camera device 230. The digital camera device (or just "camera") 230 is a forward-facing video input device that is oriented so as to cover at least a portion of a field of view (FOV) of the wearer 210. In other words, the camera 230 captures or "sees" an angle of view of the real world based on the orientation of the HMD device 220 (e.g., similar to what the wearer 210 sees in the wearer 210's FOV when looking through the visor 222). In some embodiments, output from the digital camera device 230 may be projected onto the visor 222 (e.g., in opaque visor embodiments), and may also include additional digital content (e.g., added to the camera output).

In some embodiments, the HMD device 220 may include one or more sensors 112, or may be coupled in wired or wireless communication with the sensors 112 (e.g., near-field communication (NFC) with a wrist-wearable device also worn by the wearer 210).

During operation, the HMD device 220 is mounted over both eyes 214 of the wearer 210, as shown in FIG. 2. In the example embodiment, the HMD device 220 presents various stimuli, such as the baseline stimuli 122 or the real-world stimuli 130, to the wearer 210, and may collect sensor data from sensors 112 and transmit that sensor data to the anxiety evaluation engine 120. In other embodiments, the HMD device 220 may be communicatively coupled to the user computing device 104, and may act as the display device 106, the audio device 108, the input device 110, or one or more of the sensors 112.

In some embodiments, the camera 230 may be used to capture digital content associated with the real-world stimuli 130 during daily life of the wearer 210. For example, the wearer 210 may be reading non-digital content, such as a physical magazine or newspaper, or witnessing a real-world event, such as a long line at airport security, or consuming content not provided by the user computing device 104, such as watching a cable news program on a friend's television. As such, the camera 230 may capture digital video of the real-world environment as the wearer 210 experiences the stimuli, thereby providing another avenue for the real-world stimuli 130.

Experiencing the various stimuli 122, 130 through the HMD device 220 may provide the wearer 210 with a more immersive experience and, as such, may cause the wearer 210 to exhibit more pronounced or authentic physiological responses to the stimuli 122, 130. Further, some types of stimuli 122, 130 may leverage benefits of VR or AR (e.g., virtual environments) and, as such, the HMD device 220 provides additional ways to expose the wearer 210 to different types of stimuli. This may be useful for users 102 with differing physical abilities and opportunities.

While the examples shown and described herein are illustrated with respect to a VR-based HMD device 220, it should be understood that many of the systems and methods described herein may be applied to an AR-based HMD.

Figure 3:
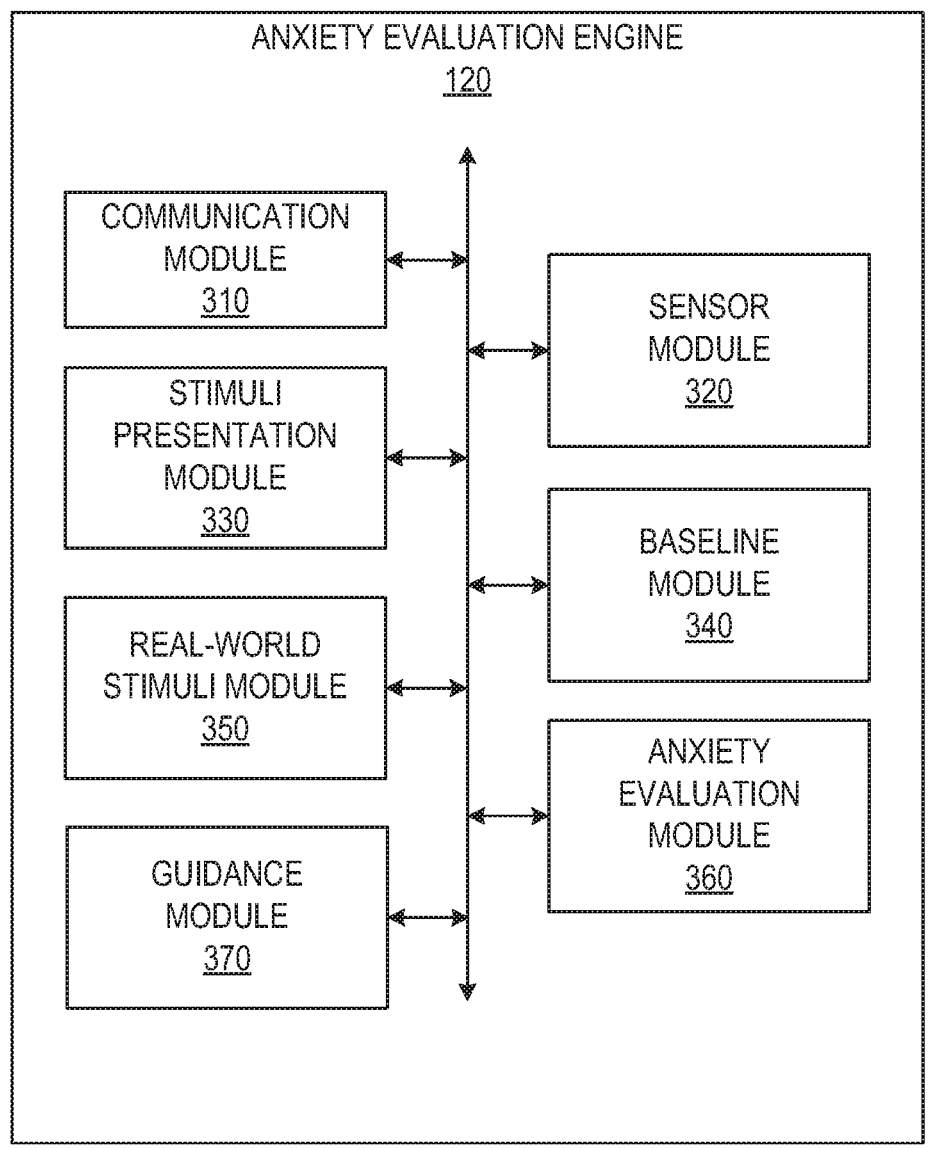
FIG. 3 is a block diagram showing components within the anxiety evaluation engine, according to some embodiments.

FIG. 3 is a block diagram showing components within the anxiety evaluation engine 120, according to some embodiments. The anxiety evaluation engine 120 may be hosted on dedicated or shared server machines (not shown) that are communicatively coupled to facilitate communications between the server machines. The components themselves may be communicatively coupled to each other and to various data sources, so as to allow information to be passed among the components or so as to allow the components to share and access common data. Furthermore, the components may access one or more databases (e.g., baseline stimuli 122, user data 124) via database servers (not separately shown). In the example embodiment, the anxiety evaluation engine 120 includes a communication module 310, a sensor module 320, a stimuli presentation module 330, a baseline module 340, a real-world stimuli module 350, an anxiety evaluation module 360, and a guidance module 370.

The communication module 310, in an example embodiment, provides network communication functionality between the anxiety evaluation engine 120 and other computing devices, such as the user computing device 104 or the HMD device 220. In some embodiments, the communication module 310 facilitates communication over the Internet or other Internet Protocol (IP) based networks (e.g., IEEE 802 standards). In some embodiments, the communication module 310 facilitates communication to devices over cellular networks (e.g., to smartphone or tablet devices over a 3G/4G network). In other embodiments, the communication module 310 allows the anxiety evaluation engine 120 to communicate over both IEEE 802 standard-based network and a cellular network at the same time (e.g., connects to the inquiring user computing device 104 over the cellular network and connects to third-party websites over the 802 network).

In an example embodiment, the sensor module 320 provides biometric sensor data of the user 102 from sensors 112. The biometric sensor data may come from a variety of types of sensors. The sensor module 320 may provide raw data values from the sensors 112, or may provide normalized values. The stimuli presentation module 330 presents baseline stimuli 122, and in some cases real-world stimuli 130, to the user 102, thereby causing physiological reactions in the user 102, and subsequent biometric sensor data from the sensors 112.

The baseline module 340 evaluates sensor data of the user 102 from the sensor module 320 and computes baseline anxiety values for the user 102. Baseline anxiety values may include, for example, individual reading measures, a mean or median anxiety score from baseline generic stimuli 122A, a mean or median anxiety score from baseline target stimuli 122B, a combined average baseline anxiety score from all baseline stimuli 122, a high score, low score, or score range for baseline generic stimuli 122A, baseline target stimuli 122B, or combined for all baseline stimuli 122. Any or all of these scores associated with the user 102 may be stored as a part of baseline user data 124A.

The real-world stimuli module 350 detects the occurrence of real-world stimuli 130 and coordinates capture of content associated with the real-world stimuli 130 and sensor data from the sensor module 320 contemporaneous with the user 102 experiencing the real-world stimuli 130. The real-world stimuli module 350 may also analyze that sensor data to determine whether the real-world stimuli 130 represent generic stimuli or target subject matter stimuli. The real-world stimuli module 350 may store the data associated with the real-world stimuli 130 as associated with the user 102 in the historical user data 124B, and may update baseline values of the user 102 based on the real-world stimuli 130.

The anxiety evaluation module 360 uses the anxiety values to evaluate risk tolerance of the user 102. In some embodiments, the anxiety evaluation module 360 evaluates risk tolerance of the user 102 specifically relative to the target subject matter. For example, the target subject matter may be financial investing (e.g., stimuli that are related to a financial portfolio of the user 102). From the anxiety scores, the anxiety evaluation module 360 may compute a risk tolerance category for the user 102, such as "high risk tolerance", "medium risk tolerance", and "low risk tolerance", representing a classification of the user 102 related to how comfortable they are with risk in financial investing. Someone with a relatively high average anxiety score (e.g., relative to other users 102 evaluated by the anxiety evaluation module 360) for the target subject matter may be categorized as "low risk tolerance" because they reacted strongly to the stimuli 122, 130. For example, the user 102 may exhibit high anxiety when presented with baseline stimuli showing business news regarding market volatility, or when presented with real-world stimuli as they discover that their portfolio has lost 5% value since last they viewed their portfolio. On the other hand, someone with a low average anxiety score for the target subject matter may be categorized as "high risk tolerance" because they did not react so dramatically to the stimuli 122, 130, thereby demonstrating some level of comfort with risk, or some level of resistance to negative effects of risk. This risk tolerance result for the user 102 may be presented to a financial advisor for the user 102, who may subsequently alter investment advice based on the categorization of the user 102.

The guidance module 370, in some embodiments, uses the risk tolerance result to automatically provide financial advice to the user 102. For example, the guidance module 370 may recommend a portfolio position for the user 102 based on the risk tolerance result. The guidance module 370 may include a set of pre-defined portfolio recommendations, one for each category of risk tolerance. For example, a "low risk tolerance" portfolio recommendation may include recommending the user 102 be 50% in lower risk investments (e.g., fixed income or low volatility equities) and 50% in higher risk investments (e.g., stocks, emerging markets). A "medium risk tolerance" portfolio recommendation may include shifting those positions to 40% low risk investments and 60% higher risk investments. A "high risk tolerance" portfolio recommendation may include shifting those positions to 30% low risk investments and 70% higher risk investments. In some embodiments, the recommendation may be presented to the user 102.

Figure 4:
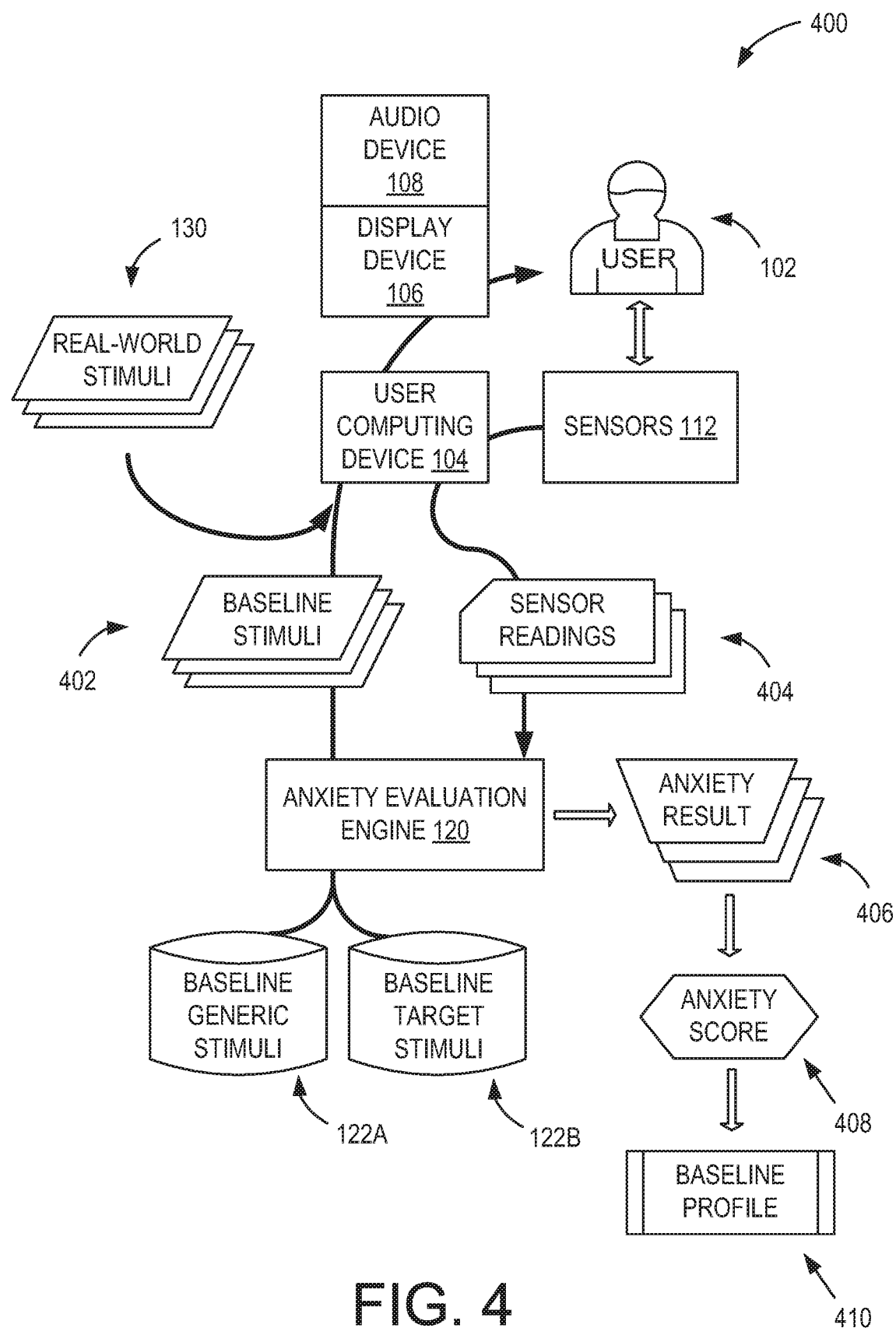
FIG. 4 is an illustration of an example baseline process in which the anxiety evaluation engine presents baseline stimuli to the user to generate a baseline profile for the user.

FIG. 4 is an illustration of an example baseline process 400 in which the anxiety evaluation engine 120 presents baseline stimuli 402 to the user 102 to generate a baseline profile 410 for the user 102. In the example embodiment, the user 102 is a person having an investment portfolio managed by a financial entity (not separately depicted), and the target subject matter is financial investing. Subject matter for financial investing may include matters relating to investing in general (e.g., stock and bond markets and associated indices, investment services, common investment practices), or to particular aspects of investing (e.g., market news, company news and performance, international markets, commodities, stocks, bonds), or matters relating to the investment portfolio of the user 102 (e.g., performance of particular investments in the user's portfolio, or news of associated companies or related industries). Some specific examples include showing news clips when stock markets decline or rise significantly, or showing the user's 102 portfolio after hypothetical market fluctuations. These may be depicted through showing hypothetical account balance changes, bar or line charts depicting portfolio fluctuations, or tangible items that may or may not be affordable after portfolio moves.

Some known investment systems implement human or automated advisors that evaluate risk tolerance of their investors based on a risk tolerance questionnaire. These questionnaires often include a series of questions designed to gauge the investor's willingness to take risks, such as through example scenarios (e.g., likes or dislikes taking risks, level of anxiety when components of their portfolio are impacted by day-to-day fluctuations and such, appreciates the potential rewards relative to the potential risks of particular investments, and so forth). However, such questionnaires may yield poor predictions of how the investor really feels. Some such misevaluation may result, for example, because of the self-provided nature of the questionnaires. In other words, the answers given by the investor may not accurately reflect how they would really feel when actually experiencing the fact pattern given by an example scenario. As such, such a questionnaire-based risk tolerance evaluation of the investor may provide an inaccurate evaluation of the investor's true risk tolerance. For example, questionnaires may be too short, confusing, not taken seriously, or not elicit consistent or accurate responses. Questionnaires may not command the attention they deserve and they ask individuals to forecast how they will feel (e.g., prospection), which may be prone to error.

In an example embodiment, the anxiety evaluation engine 120 avoids some of the known problems with some known systems by, among other things, capturing and evaluating physiological responses of the investor (e.g., the user 102) through various biometric sensors 112 as they experience baseline stimuli 122 or real-world stimuli 130. Such an evaluation may provide more accurate response data as, for example, physiological responses are generally subconscious, or reflexive in nature, rather than conscious, thought-out responses of the investor. Further, the authenticity of physiological responses is improved by providing stimuli 122, 130 to the user 102 that are more realistic, or better suited to generate physiological reactions while experiencing the stimuli 122, 130. For example, baseline stimuli 122 may leverage AR or VR for an immersive, sensory experience, or multi-media experiences including audio, images, or video, or virtual game-based environments. Such stimuli generally provide more authentic physiological responses from the user 102 than simple, text-based questions. The responses may also be more nuanced, as questionnaires may not ask, for example, five questions and categorize individuals into more than five risk-tolerance categories. The system 100 may allow for placing individuals across a continuum of risk tolerance.

In an example embodiment, the anxiety evaluation engine 120 generates a baseline profile 410 based on sensor readings 404 taken from the user 102 as they experience a set of baseline stimuli 402. During the baseline process 400, each baseline stimulus 402 is presented to the user 102 one at a time. In an example embodiment, the baseline stimuli 402 are transmitted to the user computing device 104, and the user computing device 104 (e.g., via a client application of the anxiety evaluation engine 120) presents the baseline stimuli 402 to the user 102 (e.g., via the display device 106, the audio device 108, and so forth). While the user 102 is experiencing the each baseline stimulus 402, the sensor(s) 112 capture one or more sensor readings 404 from the user 102. The sensor readings 404 are sent to the anxiety evaluation engine 120. The anxiety evaluation engine 120 may store the sensor readings 404 in the baseline user data 124A. The anxiety evaluation engine 120 uses the sensor readings 404 to generate the baseline profile 410 for the user 102.

More specifically, in an example embodiment, the anxiety evaluation engine 120 selects the set of baseline stimuli 402 from the baseline generic stimuli 122A and the baseline target stimuli 122B, where the baseline target stimuli 122B relate to aspects of financial investing. The baseline stimuli 402 include a subset of baseline generic stimuli 122A not directly related to financial investing and a subset of baseline target stimuli 122B related to financial investing. As such, each baseline stimulus 122 is identifiable as either a generic stimulus 122A or a target stimulus 122B.

In some embodiments, the set of baseline stimuli 402 may be pre-determined (e.g., identified by a human analyst prior to the baseline process 400). Further, each baseline stimulus 402 may also be pre-classified (e.g., by the analyst) as either generic or related to the target subject matter. For example, the analyst may create baseline stimuli 122, and may also identify an estimated anxiety level for each baseline stimuli 122. Some stimuli 122 may generally be thought to generate little anxiety in the average viewer. For example, a picture of a beautiful sunset or a cute puppy dog may be classified as "low anxiety" generic stimuli 122A, a video of a sports event or a traffic jam may be classified as "medium anxiety" generic stimuli 122A, and a VR simulation of someone screaming directly at the viewer or of the viewer riding a virtual roller coaster may be classified as "high anxiety" generic stimuli 122A. Similarly, with regard to target stimuli 122B, an image of a person with cash in their hand and a smile on their face may be classified as a "low anxiety" target stimuli 122B, a video of a news program depicting the Dow Jones Industrial Average (DJIA) index down 1% during a trading day, or of the "U.S. Debt Clock" for the U.S. federal debt shown increasing, may be classified as a "medium anxiety" target stimuli 122B, and a VR simulation of a portfolio down 20% amid economic news of a market crashing may be classified as a "high anxiety" target stimuli 122B.

The analyst may select baseline stimuli 402 such as to provide a breadth of experience for the user 102 across the range of estimated anxiety levels. For example, the analyst may select a number of high, medium, and low generic or target stimuli 122 in order to elicit varied physiological responses from the user 102. As such, the sensor readings 404 may yield a better range of responses showing, for example, a more accurate average or range of anxiety responses particular to the user 102. Because "priming" is an issue in biometric measurement, whereby an individual already in a high anxiety state may stay in that state even if presented with low anxiety inducing stimuli, the system 100 may present various stimuli in a variety of orders or permutations to control for priming.

In some embodiments, the anxiety evaluation engine 120 may automatically select the baseline stimuli 402 from the pool of generic stimuli 122A and target stimuli 122B. For example, the anxiety evaluation engine 120 may randomly select a pre-determined number of baseline generic stimuli 122A from each anxiety category "low", "medium", and "high", as well as a pre-determined number of baseline target stimuli 122B from each of anxiety category "low", "medium", and "high". In some embodiments, the baseline stimuli 402 may be restricted based on the hardware platform available to the user 102 (e.g., the limitations of the user computing device 104). For example, if the user computing device 104 does not include VR functionality, then the anxiety evaluation engine 120 may exclude VR-based baseline stimuli 122. In some embodiments, the baseline stimuli 402 may favor certain types of stimuli. For example, if the user computing device 104 supports VR, then selection of baseline stimuli 402 may favor VR-based stimuli 122 over non-VR-based stimuli 122 as, for example, they may provide a more pronounced or authentic experience for the user 102, and thus a more realistic physiological reaction.

In an example embodiment, the anxiety evaluation engine 120 collects baseline anxiety results 406 based on the sensor readings 404. The "raw" sensor readings captured from the sensors 112 may differ based on the particular type of sensor generating the reading 404. For example, a wristband may record pulse rate and changes in pulse rate (e.g., in beats per minute), temperature sensors may detect user temperature and changes in temperature (e.g., in Fahrenheit, Celsius, or Kelvin), while other sensors may detect salinity (e.g., in parts per million) as a measure of perspiration. As such, computation of baseline anxiety results 406 may also be dependent on the type of sensor 112, how the sensor 112 is configured to generate results, or how that type of sensor 112 is used as a proxy for evaluating anxiety.

Some types of sensors 112 generate a raw value or series of raw values for each particular stimulus 402, 130, and in a particular unit of measure based on the type of sensor 112. For example, while presenting a single baseline stimulus 402, some sensors 112 may be configured to poll once to capture a single raw value (e.g., at a pre-determined amount of time after beginning presentation of the baseline stimulus 402, such as 2 seconds after starting presentation, or at a particular time during the baseline stimulus 402, such as at a pre-identified time when anxiety is anticipated to be highest based on the content of the particular baseline stimulus 402). Some sensors may be configured to poll multiple times, generating multiple raw values for a single stimulus 402 (e.g., a pre-determined number of times during the presentation, such as every 0.5 seconds (s) for the first 10 seconds of the stimulus 402, or at multiple pre-identified times, such as at several times when anxiety is anticipated to be highest based on the content of the particular stimulus 402).

In some embodiments, the anxiety evaluation engine 120 may use a single sensor reading 404 for a particular stimulus 402, 130 as an anxiety result 406 for that stimulus 402, 130. In some embodiments, the anxiety evaluation engine 120 may reduce multiple sensor readings 404 for a particular stimulus 402 down to a single anxiety result 406 for that stimulus 402, 130. For example, the anxiety evaluation engine 120 may select the highest or lowest sensor reading from the multiple sensor readings 404 for that particular stimulus 402, or may determine a mean, median, or mode from the multiple sensor readings 404 as the anxiety result 406 for that particular stimulus 402, 130. In some embodiments, the anxiety evaluation engine 120 may determine an anxiety range for the multiple sensor readings 404 as the anxiety result 406 for that particular stimulus 402.

In some embodiments, sensor readings 404 may be normalized based on the type of sensor 112 generating the particular reading 404. Because different types of sensors 112 may be used to evaluate anxiety and, as such, may generate readings 404 that are compared to each other, normalization allows sensor readings 404 from different types of sensors 112 to be used together. In other words, normalization based on sensor type effectively maps sensor readings 404 onto a shared scale, where similar normalized values represent similar anxiety evaluations. Normalization may involve various statistical ways of controlling for or eliminating outlier or errant readings.

As such, each baseline stimulus 402 generates an associated anxiety result 406. In an example embodiment, the anxiety evaluation engine 120 uses the set of anxiety results 406 from all of the baseline stimuli 402 to generate an anxiety score 408. In some embodiments, the anxiety evaluation engine 120 may compute the anxiety score 408 as a mean, median, or mode of the anxiety results 406, or as the highest or lowest anxiety result 406. In other embodiments, the anxiety score 408 may be an average or statistical measure of a central tendency of a subset of the anxiety results 406, such as the average of the highest 20% of anxiety results 406.

In some embodiments, the anxiety evaluation engine 120 may alternatively or additionally generate an anxiety range (not separately depicted) from the anxiety results 406. For example, the anxiety results 406 may define a range based on the highest anxiety result 406, the lowest anxiety result 406, and optionally any anxiety ranges within the anxiety results 406, each of which includes an associated high and low.

In an example embodiment, the anxiety evaluation engine 120 builds a baseline profile 410 for the user 102 using the anxiety score 408, and optionally the anxiety results 406 and the anxiety range.

In an example embodiment, the anxiety evaluation engine 120 uses anxiety results 406 from generic stimuli 122A and target stimuli 122B to compute a "combined" anxiety score 408. In some embodiments, the anxiety evaluation engine 120 may compute an anxiety score 408 based on only the sensor readings 404 from the generic stimuli 122A (referred to herein as a "generic anxiety score", not separately depicted). In some embodiments, the anxiety evaluation engine 120 may compute an anxiety score 408 based on only the sensor readings 404 from the target stimuli 122B (referred to herein as a "target anxiety score", not separately depicted). As such, the baseline profile 410 for the user 102 may include one or more of a combined anxiety score 408, a generic anxiety score 408, and a target anxiety score 408.

In some embodiments, the anxiety evaluation engine 120 may also modify the anxiety score 408 based on the real-world stimuli 130. For example, after creating a baseline anxiety score 408, the anxiety evaluation engine 120 may later monitor for occurrence of real-world stimuli 130. Upon detecting that the user 102 is experiencing a particular real-world stimulus 130, the anxiety evaluation engine 120 may receive sensor readings 404 from the sensors 112. Similar to the baseline process 400, the anxiety evaluation engine 120 may generate additional anxiety results 406 based on the sensor readings 404 from that real-world stimulus 130. The anxiety evaluation engine 120 may then re-compute the anxiety score 408 for the user 102, for example using the baseline anxiety results 406 and the additional anxiety result(s) 406 from the real-world stimuli 130. In some embodiments, the anxiety results 406 from the real-world stimuli 130 may be weighted higher relative to the baseline stimuli 122 as, for example, the real-world stimuli 130 may generate more authentic physiological responses from the user 102.

Figure 5:
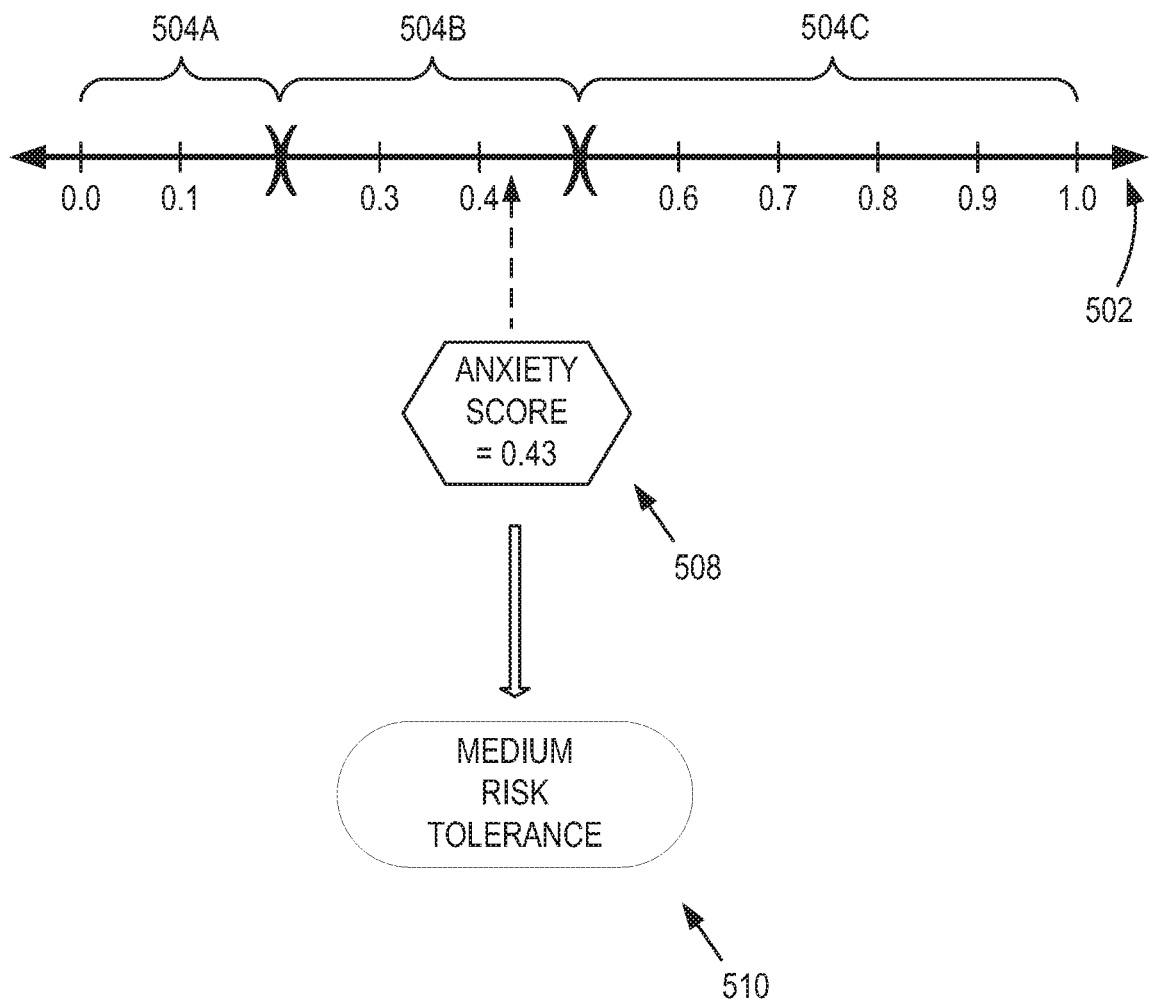
FIG. 5 is a number line illustrating an example set of three risk tolerance ranges that may be used to evaluate risk tolerance using an anxiety score of the user.

FIG. 5 is a number line 502 illustrating an example set of three risk tolerance ranges 504A, 504B, 504C that may be used to evaluate risk tolerance using an anxiety score 508 of the user 102. In some embodiments, the anxiety score 508 may be similar to the anxiety score 408. In an example embodiment, the anxiety evaluation engine 120 uses the three risk tolerance ranges 504A, 504B, 504C (collectively, risk tolerance ranges 504) to evaluate risk tolerance of users such as the user 102. The three risk tolerance ranges 504 may represent "low", "medium", and "high" risk tolerance, respectively. Each of the ranges 504 defines non-overlapping boundaries on the number line 502. In an example embodiment, "low" risk tolerance is defined by range 504A between 0.0 and 0.2, "medium" risk tolerance is defined by range 504B between 0.2 and 0.5, and "high" risk tolerance is defined by range 504C between 0.5 and 1.0.

In an example embodiment, the anxiety evaluation engine 120 defines the user 102's risk tolerance result 510 based on the particular range 504 within which the user 102's anxiety score 508 falls. In this example, the anxiety score 508 of the user 102 is 0.43. As such, the anxiety evaluation engine 120 rates the user 102 as a "medium" risk tolerance result 510.

In some embodiments, the boundaries of each range 504 of risk tolerance may be pre-defined. For example, an analyst may identify the ranges 504 as depicted in FIG. 5. In some embodiments, the ranges 504 may be automatically determined. For example, the ranges 504 may be determined based on multiple anxiety scores 408 for multiple users 102. The anxiety evaluation engine 120 may set the boundaries of the ranges 504 such that a pre-defined percentage of users 102 falls within each range 504, based on their associated anxiety scores 408. For example, the boundaries of the ranges 504 may be set such that the lowest 33% of users 102 fall within the "low" range 504A, the middle 33% of users 102 fall within the "middle" range 504B, and the top 33% of users 102 fall within the "high" range 504C. Or the boundaries may be set to 40% "low", 40% "middle", and 20% "high". The anxiety score 408 from the target stimuli 122B are mapped onto the spectrum developed from the generic stimuli 122A to identify where, for example, different portfolios of financial investments fall. This should help individuals or their financial advisors select appropriate portfolios. This information can also be used when an individual is logging into their investment account for purposes of conducting a transaction. The user's emotional state may be transmitted to the financial firm, which may generate warnings, or may restrict certain types of activities, based on the user's emotional state.

Once the risk tolerance result 510 of the user 102 has been determined, the anxiety evaluation engine 120 provides the risk tolerance result 510 for use in providing investment advice for the user 102. In some embodiments, the risk tolerance result 510 may be provided to a financial advisor for the user 102. In some embodiments, the risk tolerance result 510 may be provided directly to the user 102 (e.g., through a display dashboard).

In some embodiments, the anxiety evaluation engine 120 may automatically provide investment advice to the user 102 based on the risk tolerance result 510. For example, the anxiety evaluation engine 120 may include pre-defined investment advice for each range 504. The advice may be based on a percentage distribution of the user 102's investment portfolio, such as recommending the user 102 distribute their investments into 50% safer investments (e.g., fixed income, cash) and 50% in more speculative investments (e.g., stocks) if "low" risk tolerance, or 40% safer investments and 60% speculative investments if "medium" risk tolerance, or 30% safer investments and 70% speculative investments if "high" risk tolerance.

Figure 6:
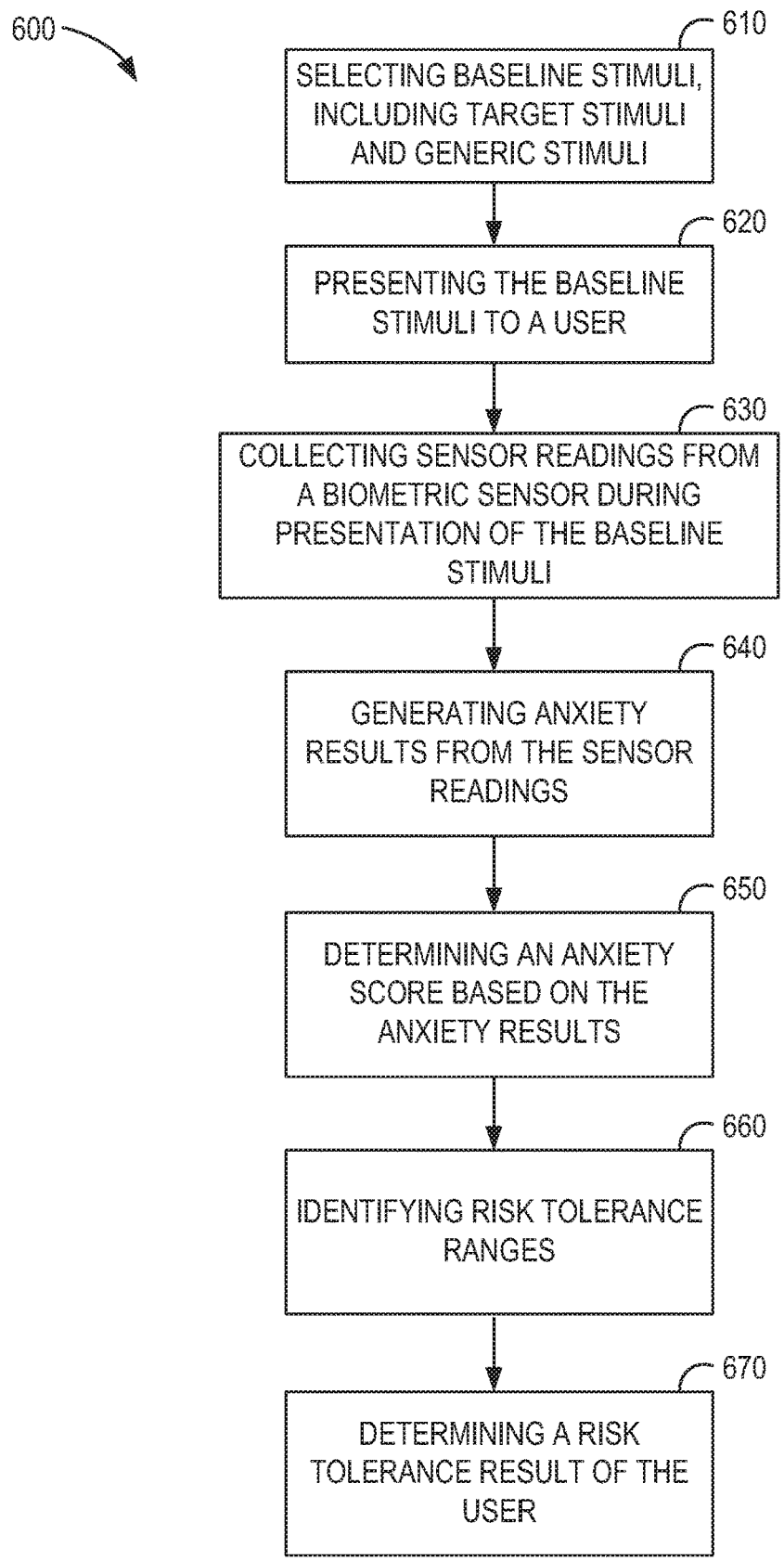
FIG. 6 illustrates an example computer-implemented method for evaluating risk tolerance of the user.

FIG. 6 illustrates an example computer-implemented method 600 for evaluating risk tolerance of the user 102. The computer-implemented method 600, hereafter referred to as "the method 600," is performed by a computing device comprising at least one hardware processor and a memory. In an example embodiment, the method 600 includes selecting a plurality of stimuli from a pool of stimuli, the selected plurality of stimuli including at least one target stimulus associated with a subject matter and at least one generic stimulus not directly associated with the subject matter (see operation 610). In some embodiments, selecting a plurality of stimuli further includes selecting a virtual reality-based stimulus, wherein presenting each stimulus further includes presenting the virtual reality-based stimulus to the user via a head-mounted display.

The method 600 also includes presenting each stimulus of the plurality of stimuli to a user (see operation 620). The method 600 further includes, during presentation of each stimulus, collecting sensor readings from a biometric sensor, the biometric sensor being configured to detect physiological data associated with the anxiety of the user (see operation 630). In some embodiments, a first stimulus of the plurality of stimuli includes a sensor timing mark identifying a point in time within the first stimulus, and collecting sensor readings further includes collecting a first sensor reading from the sensor at the sensor timing mark.

The method 600 also includes generating a plurality of anxiety results from the sensor readings, each stimulus of the plurality of stimuli having an associated anxiety result (see operation 640). The method 600 further includes determining an anxiety score based on the plurality of anxiety results (see operation 650). The method 600 also includes identifying a plurality of risk tolerance ranges, each risk tolerance range of the plurality of risk tolerance ranges being associated with a category of risk tolerance (see operation 660). The method 600 further includes determining a risk tolerance result of the user based on comparing the anxiety score to the plurality of risk tolerance ranges (see operation 670).

In some embodiments, the method 600 further includes generating a target anxiety score using only the target stimuli. In some embodiments, collecting sensor readings further includes collecting a plurality of sensor readings associated with a first stimulus of the plurality of stimuli, and generating a plurality of anxiety results further includes generating a first anxiety result associated with the first stimulus based on the plurality of sensor readings. In some embodiments, the method 600 further includes collecting at least one sensor reading from the sensor as the user is experiencing a real-world stimulus, generating a first anxiety result from the at least one sensor reading, and altering the anxiety score based on the first anxiety result. In some embodiments, the target subject matter is financial investing.

Figure 7:
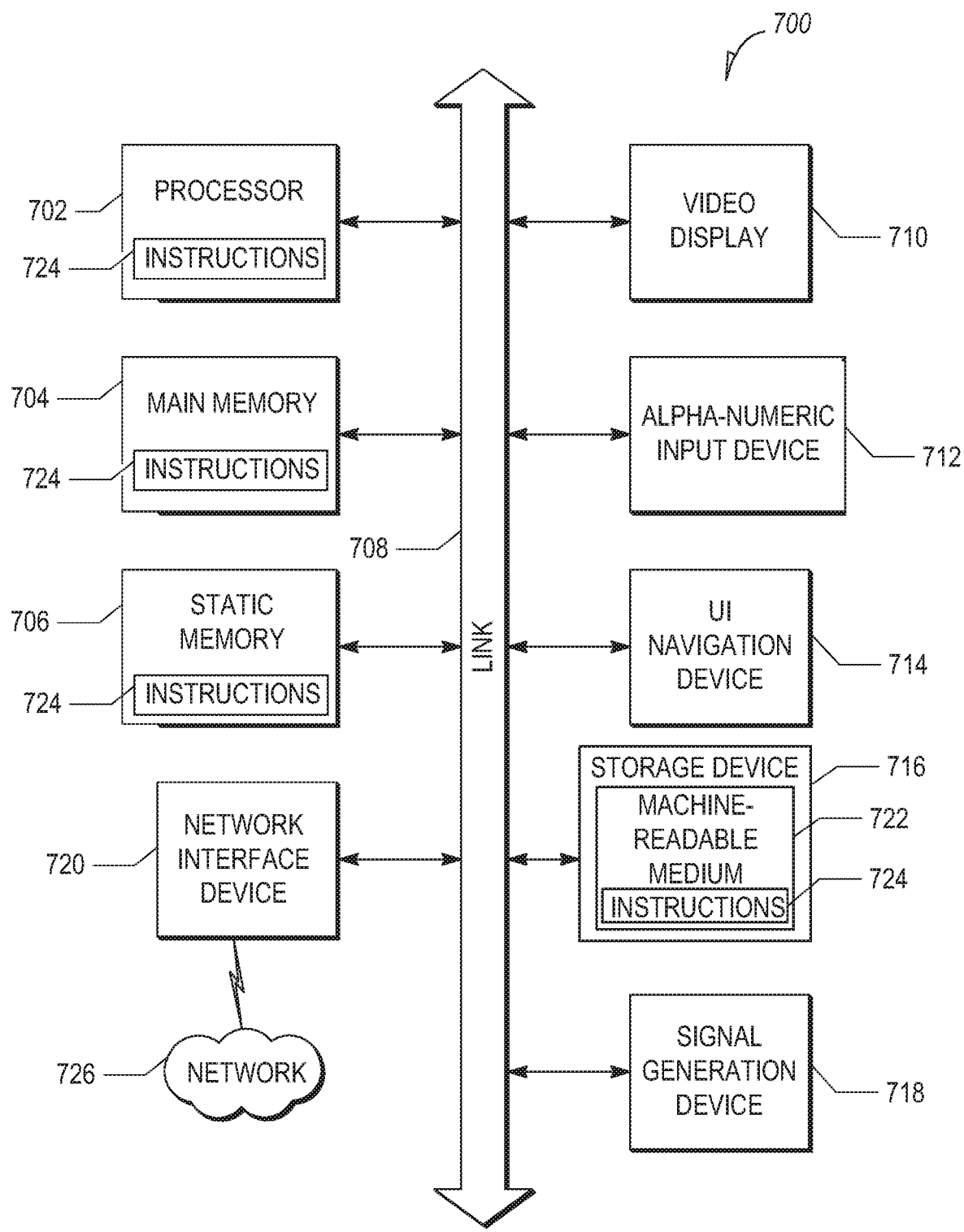
FIG. 7 is a block diagram illustrating a machine in the example form of a computer system, within which a set or sequence of instructions can be executed to cause the machine to perform any one of the methodologies discussed herein, according to an example embodiment.

FIG. 7 is a block diagram illustrating a machine in the example form of a computer system 700, within which a set or sequence of instructions can be executed to cause the machine to perform any one of the methodologies discussed herein, according to an example embodiment. In alternative embodiments, the machine operates as a standalone device or can be connected (e.g., networked) to other machines. In a networked deployment, the machine can operate in the capacity of either a server or a client machine in server-client network environments, or it can act as a peer machine in peer-to-peer (or distributed) network environments. The machine can be a personal computer (PC), a tablet PC, a hybrid tablet, a set-top box (STB), a personal digital assistant (PDA), a mobile telephone, a web appliance, a network router, switch or bridge, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein.

The example computer system 700 includes at least one processor 702 (e.g., a central processing unit (CPU), a graphics processing unit (GPU) or both, processor cores, compute nodes, etc.), a main memory 704 and a static memory 706, which communicate with each other via a link 708 (e.g., bus). The computer system 700 can further include a video display unit 710, an alphanumeric input device 712 (e.g., a keyboard), and a user interface (UI) navigation device 714 (e.g., a mouse). In one embodiment, the video display unit 710, alphanumeric input device 712, and UI navigation device 714 are incorporated into a touch-screen display. The computer system 700 can additionally include a storage device 716 (e.g., a drive unit), a signal generation device 718 (e.g., a speaker), a network interface device 720, and one or more sensors (not shown), such as a global positioning system (GPS) sensor, compass, accelerometer, or other sensor.

The storage device 716 includes a machine-readable medium 722 on which is stored one or more sets of data structures and instructions 724 (e.g., software) embodying or utilized by any one or more of the methodologies or functions described herein. The instructions 724 can also reside, completely or at least partially, within the main memory 704, within the static memory 706, and/or within the processor 702 during execution thereof by the computer system 700, with the main memory 704, static memory 706, and the processor 702 also constituting machine-readable media.

While the machine-readable medium 722 is illustrated in an example embodiment to be a single medium, the term "machine-readable medium" can include a single medium or multiple media (e.g., a centralized or distributed database, and/or associated caches and servers) that store the one or more instructions 724. The term "machine-readable medium" shall also be taken to include any tangible medium that is capable of storing, encoding, or carrying instructions (e.g., instructions 724) for execution by the machine and that cause the machine to perform any one or more of the methodologies of the present disclosure or that is capable of storing, encoding, or carrying data structures utilized by or associated with such instructions. The term "machine-readable medium" shall accordingly be taken to include, but not be limited to, solid-state memories, and optical and magnetic media. Specific examples of machine-readable media include non-volatile memory, including, but not limited to, by way of example, semiconductor memory devices (e.g., electrically programmable read-only memory (EPROM), electrically erasable programmable read-only memory (EEPROM)) and flash memory devices; magnetic disks such as internal hard disks and removable disks; magneto-optical disks; and CD-ROM and DVD-ROM disks.

The instructions 724 can further be transmitted or received over a communications network 726 using a transmission medium via the network interface device 720 utilizing any one of a number of well-known transfer protocols (e.g., HTTP). Examples of communication networks include a local area network (LAN), a wide area network (WAN), the Internet, mobile telephone networks, plain old telephone service (POTS) networks, and wireless data networks (e.g., Wi-Fi, 3G, and 6G LTE/LTE-A or WiMAX networks). The term "transmission medium" shall be taken to include any intangible medium that is capable of storing, encoding, or carrying instructions for execution by the machine, and includes digital or analog communications signals or other intangible media to facilitate communication of such software.

The above description is intended to be illustrative, and not restrictive. For example, the above-described examples (or one or more aspects thereof) can be used in combination with others. Other embodiments can be used, such as by one of ordinary skill in the art upon reviewing the above description. The Abstract is to allow the reader to quickly ascertain the nature of the technical disclosure, for example, to comply with 37 C.F.R. § 1.72(b) in the United States of America. It is submitted with the understanding that it will not be used to interpret or limit the scope or meaning of the claims.

Also, in the above Detailed Description, various features may be grouped together to streamline the disclosure. However, the claims may not set forth every feature disclosed herein as embodiments can feature a subset of said features. Further, embodiments can include fewer features than those disclosed in a particular example. Thus, the following claims are hereby incorporated into the Detailed Description, with each claim standing on its own as a separate embodiment. The scope of the embodiments disclosed herein is to be determined with reference to the appended claims, along with the full scope of equivalents to which such claims are entitled.

What is claimed is:

1. A system comprising:
   a biometric sensor configured to detect physiological data associated with anxiety of a user;
   at least one hardware processor; and
   a memory storing instructions that, when executed by the at least one hardware processor, cause the at least one hardware processor to perform operations comprising:
      selecting a plurality of stimuli from a pool of stimuli, the selected plurality of stimuli including at least one target stimulus associated with a subject matter and at least one generic stimulus not directly associated with the subject matter;
      generating visual and audio outputs for each stimulus of the plurality of stimuli;
      presenting the visual and audio outputs for each stimulus of the plurality of stimuli to the user via a display device and a speaker of a computing device, respectively;
      during presentation of each stimulus, collecting sensor readings from the biometric sensor, in response to presentation of the visual and audio outputs;
      generating a plurality of anxiety results from the sensor readings, each stimulus of the plurality of stimuli associated with an anxiety result;
      determining an anxiety score based on the plurality of anxiety results;

identifying a plurality of risk tolerance ranges, each risk tolerance range of the plurality of risk tolerance ranges being associated with a category of risk tolerance; and determining a risk tolerance result of the user based on comparing the anxiety score to the plurality of risk tolerance ranges.

2. The system of claim 1, wherein selecting the plurality of stimuli further includes selecting a virtual reality-based stimulus, wherein presenting each stimulus further includes presenting the virtual reality-based stimulus to the user via a head-mounted display.

3. The system of claim 1, wherein the operations further comprise generating a target anxiety score using only target stimuli.

4. The system of claim 1, wherein a first stimulus of the plurality of stimuli includes a sensor timing mark identifying a point in time within the first stimulus, wherein collecting the sensor readings further includes collecting a first sensor reading from the biometric sensor at the sensor timing mark.

5. The system of claim 1, wherein collecting the sensor readings further includes collecting a plurality of sensor readings associated with a first stimulus of the plurality of stimuli, wherein generating the plurality of anxiety results further includes generating a first anxiety result associated with the first stimulus based on the plurality of sensor readings.

6. The system of claim 1, wherein the operations further comprise:
collecting at least one sensor reading from the biometric sensor as the user is experiencing a real-world stimulus;
generating a first anxiety result from the at least one sensor reading; and
altering the anxiety score based on the first anxiety result.

7. The system of claim 1, wherein the subject matter is financial investing.

8. A computer-implemented method comprising:
selecting a plurality of stimuli from a pool of stimuli, the selected plurality of stimuli including at least one target stimulus associated with a subject matter and at least one generic stimulus not directly associated with the subject matter;
generating visual and audio outputs for each stimulus of the plurality of stimuli;
presenting the visual and audio outputs for each stimulus of the plurality of stimuli to a user via a display device and a speaker of a computing device, respectively;
during presentation of each stimulus, collecting sensor readings from a biometric sensor, in response to presentation of the visual and audio outputs, the biometric sensor being configured to detect physiological data associated with the anxiety of the user;
generating a plurality of anxiety results from the sensor readings, each stimulus of the plurality of stimuli associated with an anxiety result;
determining an anxiety score based on the plurality of anxiety results;
identifying a plurality of risk tolerance ranges, each risk tolerance range of the plurality of risk tolerance ranges being associated with a category of risk tolerance; and
determining a risk tolerance result of the user based on comparing the anxiety score to the plurality of risk tolerance ranges.

9. The computer-implemented method of claim 8, wherein selecting a plurality of stimuli further includes selecting a virtual reality-based stimulus, wherein presenting each stimulus further includes presenting the virtual reality-based stimulus to the user via a head-mounted display.

10. The computer-implemented method of claim 8, further comprising generating a target anxiety score using only target stimuli.

11. The computer-implemented method of claim 8, wherein a first stimulus of the plurality of stimuli includes a sensor timing mark identifying a point in time within the first stimulus, wherein collecting the sensor readings further includes collecting a first sensor reading from the biometric sensor at the sensor timing mark.

12. The computer-implemented method of claim 8, wherein collecting the sensor readings further includes collecting a plurality of sensor readings associated with a first stimulus of the plurality of stimuli, wherein generating a plurality of anxiety results further includes generating a first anxiety result associated with the first stimulus based on the plurality of sensor readings.

13. The computer-implemented method of claim 8, the method further comprising:
collecting at least one sensor reading from the biometric sensor as the user is experiencing a real-world stimulus;
generating a first anxiety result from the at least one sensor reading; and
altering the anxiety score based on the first anxiety result.

14. The computer-implemented method of claim 8, wherein the subject matter is financial investing.

15. A non-transitory computer-readable storage medium, the computer-readable storage medium including instructions that, when executed by a computer, cause the computer to perform operations comprising:
selecting a plurality of stimuli from a pool of stimuli, the selected plurality of stimuli including at least one target stimulus associated with a subject matter and at least one generic stimulus not directly associated with the subject matter;
generating visual and audio outputs for each stimulus of the plurality of stimuli;
presenting the visual and audio outputs for each stimulus of the plurality of stimuli to a user via a display device and a speaker of a computing device, respectively;
during presentation of each stimulus, collecting sensor readings from a biometric sensor in response to presentation of the visual and audio outputs, the biometric sensor being configured to detect physiological data associated with the anxiety of the user;
generating a plurality of anxiety results from the sensor readings, each stimulus of the plurality of stimuli associated with an anxiety result;
determining an anxiety score based on the plurality of anxiety results;
identifying a plurality of risk tolerance ranges, each risk tolerance range of the plurality of risk tolerance ranges being associated with a category of risk tolerance; and
determining a risk tolerance result of the user based on comparing the anxiety score to the plurality of risk tolerance ranges.

16. The non-transitory computer-readable storage medium of claim 15, wherein selecting a plurality of stimuli further includes selecting a virtual reality-based stimulus, wherein presenting each stimulus further includes presenting the virtual reality-based stimulus to the user via a head-mounted display.

17. The non-transitory computer-readable storage medium of claim 15, wherein a first stimulus of the plurality of stimuli includes a sensor timing mark identifying a point in time within the first stimulus, wherein collecting the sensor readings further includes collecting a first sensor reading from the biometric sensor at the sensor timing mark.

18. The non-transitory computer-readable storage medium of claim 15, wherein collecting the sensor readings further includes collecting a plurality of sensor readings associated with a first stimulus of the plurality of stimuli, wherein generating a plurality of anxiety results further includes generating a first anxiety result associated with the first stimulus based on the plurality of sensor readings.

19. The non-transitory computer-readable storage medium of claim 15, wherein the operations further comprise:
   collecting at least one sensor reading from the biometric sensor as the user is experiencing a real-world stimulus;
   generating a first anxiety result from the at least one sensor reading; and
   altering the anxiety score based on the first anxiety result.

20. The non-transitory computer-readable storage medium of claim 15, wherein the subject matter is financial investing.

* * * * *

UNITED STATES PATENT AND TRADEMARK OFFICE
CERTIFICATE OF CORRECTION

PATENT NO. : 10,687,756 B1
APPLICATION NO. : 15/362489
DATED : June 23, 2020
INVENTOR(S) : Brian J. Jacobsen It is certified that error appears in the above-identified patent and that said Letters Patent is hereby corrected as shown below:

In the Claims

In Column 18, Line 43, in Claim 15, delete "sensor" and insert --sensor,-- therefor Signed and Sealed this
Twenty-third Day of March, 2021

Drew Hirshfeld
*Performing the Functions and Duties of the*
*Under Secretary of Commerce for Intellectual Property and*
*Director of the United States Patent and Trademark Office*